United States Patent [19]
Khosla et al.

[11] Patent Number: 6,066,721
[45] Date of Patent: May 23, 2000

[54] METHOD TO PRODUCE NOVEL POLYKETIDES

[75] Inventors: Chaitan Khosla, Stanford, Conn.; Rembert Pieper, Menlo Park, Calif.; Guanglin Luo; David E. Cane, both of Providence, R.I.; Camilla Kao, Palo Alto, Calif.

[73] Assignees: Stanford University, Stanford, Calif.; Brown University Research Foundation, Providence, R.I.

[21] Appl. No.: 08/896,323

[22] Filed: Jul. 17, 1997

Related U.S. Application Data

[63] Continuation-in-part of application No. 08/675,817, Jul. 5, 1996.
[60] Provisional application No. 60/003,338, Jul. 6, 1995.
[51] Int. Cl.[7] ........................... C12N 15/11; C12N 15/63; C12N 1/20
[52] U.S. Cl. .................. 536/23.1; 536/23.2; 435/320.1; 435/252.35; 435/252.3; 435/7.1
[58] Field of Search ............................. 536/23.2, 23.1; 435/7.1, 252.35, 320.1, 252.3

[56] References Cited

U.S. PATENT DOCUMENTS 5,475,099  12/1995  Knauf et al. .
5,824,513  10/1998  Katz .

FOREIGN PATENT DOCUMENTS

WO 93/13663  7/1993  WIPO .
WO 95/08548  3/1995  WIPO .

OTHER PUBLICATIONS

McDaniel, R., et al., "Gain–of–Function Mutagenesis of a Modular Polyketide Synthase," *J Am Chem Soc* (1997) 119(18):4309–4310.

Kramer, P.J., et al., "Rational Design and Engineered Biosynthesis of a Novel 18–Carbon Aromatic Polyketide," *J Am Chem Soc* (1997) 119(4):635–639.

Kao, C.M., et al., "Gain of Function Mutagenesis of the Erythromycin Polyketide Synthase. 2. Engineered Biosynthesis of an Eight–Membered Ring Tetraketide Lactone," *J Am Chem Soc* (1997) 119(46):11339–11340.

Wiesmann, K.E.H., et al., "Polyketide synthesis in vitro on a modular polyketide synthase," *Chemistry & Biology* (1995) 2(9):583–589.

Kao, C.M., et al., "Manipulation of Macrolide Ring Size by Directed Mutagenesis of a Modular Polyketide Synthase," *J Am Chem Soc* (1995) 117(35):9105–9106.

Kao, C.M., et al., "Engineered Biosynthesis of Structurally Diverse Tetraketides by a Trimodular Polyketide Synthase," *J Am Chem Soc* (1996) 118(38):9184–9185.

Donadio, S., et al., "Modular Organization of Genes Required for Complex Polyketide Biosynthesis," *Science* (1991) 252:675–679.

Donadio, S., et al., "An erythromycin analog produced by reprogramming of polyketide synthesis," *Proc Natl Acad Sci USA* (1993) 90:7119–7123.

Bedford, D., et al., "A functional chimeric modular polyketide synthase generated via domain replacement," *Chemistry & Biology* (1996) 3(10):827–831.

Oliynyk, M., et al., "A hybrid modular polyketide synthase obtained by domain swapping," *Chemistry & Biology* (1996) 3(10):833–839.

Kuhstoss, S., et al., "Production of a novel polyketide through the construction of a hybrid polyketide synthase," *Gene* (1996) 183:231–236.

(List continued on next page.)

*Primary Examiner*—Keith D. MacMillan
*Assistant Examiner*—T. D. Wessendorf
*Attorney, Agent, or Firm*—Morrison & Foerster LLP

[57] ABSTRACT

Modified PKS gene clusters which produce novel polyketides in an efficient system in a host cell or in a cell free extract are described.

12 Claims, 3 Drawing Sheets

OTHER PUBLICATIONS

Omura, et al., "Inhibition of the Biosynthesis of Leucomycin, a Macrolide Antibiotic, by Cerulenin," *J. Biochem.* 75:193–195 (1974).

Rudd, et al., "Genetics of Actinorhodin Biosynthesis by *Streptomyces Coelicolor* A3(2)," *J. Gen. Microbiol.* 114:35–43 (1979).

Donadio S, et al, (1992) Biosynthesis of the erythromycin macrolactone and a rational approach for producing hybrid macrolides. Gene 115: 97–103, 1992.

Cane DE, et al, (1993) Macrolide biosynthesis. 7. Incorporation of polyketide chain elongation intermediates into methymycin. J.Am.Chem.Soc. 115:522–526, 1993.

Kao CM, et al, (1994) Engineered biosynthesis of a complete macrolactone in a heterologous host. Science 265:509–512, 1994.

Aparicio et al., "Limited Proteolysis and Active–Site Studies of the First Multienzyme Component of the Erythromycin–Producing Polyketide Synthase," *J. of Biol. Chem.* 269(11):8524–8528 (1994).

Bartel et al., "Biosynthesis of Anthraquinones by Interspecies Cloning of Actinorhodin Biosynthesis Genes in Streptomycetes: Clarification of Actinorhodin Gene Functions," *J. Bacteriol.* 172(9):4816–4826 (1990).

Beck et al., "The Multifunctional 6–methylsalicylic Acid Synthase Gene of *Penicillium Patulum.* Its Gene Structure Relative to that of Other Polyketide Synthases," *Eur. J. Biochem.* 192:487–498 (1990).

Bevitt et al., "6–Deoxyerythronolide–B Synthase 2 from *Saccharopolyspora erythraea:* Cloning of the Structural Gene, Sequence Analysis and Inferred Domain Structure of the Multifunctional Enzyme," *Eur. J. Biochem.* 204:39–49 (1992).

Bibb et al., "Analysis of the Nucleotide Sequence of the *Streptomyces Glaucescens* tcml Genes Provides Key Information about the Enzymology of Polyketide Antibiotic Biosynthesis," *EMBO J.* 8(9):2727–2736 (1989).

Caballero et al., "Organisation and Functions of the actVA Region of the Actinorhodin Biosynthetic Gene Cluster of *Streptomyces coelicolor,*" *Mol. Gen. Genet.* 230:401–412 (1991).

Caffrey et al., "An Acyl–Carrier–Protein—Thioesterase Domain from the 6–Deoxyerythronolide B Synthase of *Saccharopolyspora erythraea.* High–Level Production, Purification and Characterisation in *Escherichia coli,*" *Eur. J. Biochem.* 195:823–830 (1991).

Caffrey et al., "Identification of DEBS 1, DEBS 2 and DEBS 3, the Multienzyme Polypeptides of the Erythromycin–Producing Polyketide Synthase from *Saccharopolyspora erythraea,*" *FEBS Lett.* 304(2):225–228 (1992).

Corcoran et al., "The Biogenesis of Fatty Acids and Erythronolide–Like Substances in Mycelium–Free Extracts of *Streptomyces Erythreus,*" in 5th International Congress of Chemotherapy, Vienna, Abstracts of Communications, pp. 35–40 (1967).

Corcoran, ed., in *Antibiotics Volume IV Biosynthesis,* Springer–Verlag, New York, pp. 145–150 (1982).

Cortes et al., "An Unusually Large Multifunctional Polypeptide in the Erythromycin–Producing Polyketide Synthase of *Saccharopolyspora erythraea,*" *Nature* 348:176–178 (1990).

Davis et al., "Functional Mapping of a Polyketide Synthase from *aspergillus terreus* involved in Lovastatin Synthesis," Abst. of the Genetics of Industrial Microorganisms Mtg. P288:192 (1994).

Dimroth et al., "Biosynthese von 6–Methylsalicylsäure," *Eur. J. Biochem.* 13:98–110 (1970).

Donadio et al., "Modular Organization of Genes Required for Complex Polyketide Biosynthesis," *Science* 252:675–679 (1991).

Donadio et al., "Organization of the Enzymatic Domains in the Multifunctional Polyketide Synthase Involved in Erythromycin Formation in *Saccharopolyspora erythraea,*" *Gene* 111:51–60 (1992).

Fernandez–Moreno et al., "The act Cluster Contains Regulatory and Antibiotic Export Genes, Direct Targets for Translational Control by the bldA tRNA Gene of Streptomyces," *Cell* 66:769–780 (1991).

Fernandez–Moreno et al., "Nucleotide Sequence and Deduced Functions of a Set of Cotranscribed Genes of *Streptomyces coelicolor* A3(2) Including the Polyketide Synthase for the Antibiotic Actinorhodin," *J. Biol. Chem.* 267:19278–19290 (1992).

Hallam et al., "Nucleotide Sequence, Transcription and Deduced Function of a Gene Involved in Polyketide Antibiotic Synthesis in *Streptomyces coelicolor,*" *Gene* 74:305–320 (1988).

Hopwood et al., "Product of 'Hybrid' Antibiotics by Genetic Engineering," *Nature* 314(6012):642–644 (1985).

Hopwood et al., "Genes for Polyketide Secondary Metabolic Pathways in Microorganisms and Plants," *Secondary Metabolites: Their Function and Evolution,* Wiley Chichester (Ciba Foundation Symposium 171), pp. 88–112 (1992).

Hunaiti et al., "Source of Methylmalonyl–Coenzyme A for Erythromycin Synthesis: Methylmalonyl–Coenzyme A Mutase from *Streptomyces erythreus,*" *Antimicrobial Agents and Chemotherapy* 25(2):173–178 (1984).

Kao et al., "Engineered Biosynthesis of a Complete Macrolactone in a Heterologous Host," *Science* 265:509–512 (1994).

Khosla et al., "Genetic Construction and Functional Analysis of Hybrid Polyketide Synthases Containing Heterologous Acyl Carrier Proteins," *J. Bacteriol.* 175(8):2197–2204 (1993).

Lanz et al., "The Role of Cysteines in Polyketide Synthase," *J. of Biol. Chem.* 266(15):9971–9976 (1991).

Leadlay et al., "The Erythromycin–Producing Polyketide Synthase," *Biochem. Soc. Transactions* 21:218–222 (1993).

MacNeil et al., "Complex Organization of the *Streptomyces avermitilis* Genes Encoding the Avermectin Polyketide Synthase," *Gene* 115:119–125 (1992).

Malpartida et al., "Molecular Cloning of the Whole Biosynthetic Pathway of a Streptomyces Antibiotic and its Expression in a Heterologous Host," *Nature* 309:462–464 (1984).

Malpartida et al., "Physical and Genetic Characterisation of the Gene Cluster for the Antibiotic Actinorhodin in *Streptomyces coelicolor* A3(2)," *Mol. Gen. Genet.* 205:66–73 (1986).

Marsden et al., "Stereospecific Acyl Transfers on the Erythromycin–Producing Polyketide Synthase," *Science* 263:378–380 (1994).

Roberts et al., "[³H]Tetrahydrocerulenin, a Specific Reagent for Radio–Labeling Fatty Acid Synthases and Related Enzymes," *FEBS Lett.* 159(1,2):13–16 (1983).

Roberts et al., "Use of [³H]Tetrahydrocerulenin to Assay Condensing Enzyme Activity in *Streptomyces erythreus*," *Biochem. Soc. Transactions* 12:642–643 (1984).

Shen et al., "Enzymatic Synthesis of a Bacterial Polyketide from Acetyl and Malonyl Coenzyme A," *Science* 262:1535–1540 (1993).

Sherman et al., "Structure and Deduced Function of the Granaticin–Producing Polyketide Synthase Gene Cluster of *Streptomyces violaceoruber* Tü22," *EMBO J.* 8(9):2717–2725 (1989).

Sherman et al., "Functional Replacement of Genes for Individual Polyketide Synthase Components in *Streptomyces coelicolor* A3(2) by Hetergenous Genes from a Different Polyketide Pathway," *J. Bacteriol.* 174 (19):6184–6190 (1992).

Spencer et al., "Purification and Properties of a 6–Methylsalicylic Acid Synthase from *Penicillium patulum*," *Biochem. J.* 288:839–846 (1992).

Wawszkiewicz et al., "Propionyl–CoA Dependent $H^{14}CO_3^-$ Exchange into Methylmalonyl–CoA in Extracts of *Streptomyces erythraeus*," *Biochemische Zeitschrift* 340:213–227 (1964).

Gokhale, R.S., et al., "Functional Orientation of the Acyltransferase Domain in a Module of the Erythromycin Polyketide Synthase", *Biochemistry* (1998) 37:2524–2528.

METHOD TO PRODUCE NOVEL POLYKETIDES

CROSS REFERENCE TO RELATED APPLICATIONS

This application is a continuation-in-part of U.S. Ser. No. 08/675,817 filed Jul. 5, 1996 which claims priority under 35 USC 119(e)(1) from provisional application Ser. No. 60/003,338 filed Jul. 6, 1995. The contents of these applications are incorporated herein by reference.

STATEMENT OF RIGHTS TO INVENTIONS MADE UNDER FEDERALLY SPONSORED RESEARCH

This invention was made with U.S. government support from the National Institutes of Health (GM22172 and CA66736-01). The government has certain rights in this invention.

TECHNICAL FIELD

The invention relates to methods to synthesize polyketides which are novel using modified modular polyketides synthases (PKS) which cannot utilize a natural first module starter unit.

BACKGROUND ART

Modular polyketide syntheses are typified by the organization of deoxyerythronolide B synthase (DEBS) which produces β-deoxyerythronolide B (6-dEB) the parent macrolactone of the broad spectrum antibiotic erythromycin. DEBS consists of three large polypeptides each containing about 10 distinctive active sites. FIG. 1 shows, diagramatically, the nature of the three DEBS modules encoded by the three genes eryAI, eryAII and eryAIII.

Various strategies have been suggested for genetic manipulation of PKS to produce novel polyketides. New polyketides have been generated through module deletion (Kao, C. M. et al., *J. Am. Chem. Soc.* (1995) 117:9105–9106; Kao, C. M. et al., *J. Am. Chem. Soc.* (1996) 118:9184–9185). Also reported to provide novel polyketides are loss of function mutagenesis within reductive domains (Donadio, S. et al., *Science* (1991) 252:675–679; Donadio, S. et el., *Proc. Natl. Acad. Sci. USA* (1993) 90:7119–7123; Bedford, D. et al., *Chem. Biol.* (1996) 3:827–831) and replacement of acyl transferase domains to alter starter or extender unit specificity (Oliynyk, M et al., *Chem. Biol.* (1996) 3:833–839; Kuhstoss, S. et al., *Gene* (1996) 183:231–236), as well as gain of function mutagenesis to introduce new catalytic activities within existing modules (McDaniel, R. et al., *J. Am. Chem. Soc.* (1997) in press). In some of these reports, downstream enzymes in the polyketide pathway have been shown to process non-natural intermediates. However, these methods for providing novel polyketides suffer from the disadvantages of requiring investment in cloning and DNA sequencing, the systems used being limited to producer organisms for which gene replacement techniques have been developed, primer and extender units that can only be derived from metabolically accessible CoA thioesters, and the fact that only limited auxiliary catalytic functions can be employed.

The DEBS system in particular has been shown to accept non-natural primer units such as acetyl and butyryl-CoA (Wiesmann, KEH et al., *Chem. Biol.* (1995) 2:583–589; Pieper, R. et al., *J. Am. Chem. Soc.* (1995) 117:11373–11374) as well as N-acetylcysteamine (NAC) thioesters of their corresponding ketides (Pieper, R. et al., *Nature* (1995) 378:263–266). However, it has become clear that even though such unnatural substrates can be utilized, competition from the natural starter unit has drastically lowered yield. Even if starter units are not supplied artificially, they can be inherently generated from decarboxylation of the methylmalonyl extender units employed by the DEBS system (Pieper, R. et al., *Biochemistry* (1996) 35:2054–2060; Pieper, R. et al., *Biochemistry* (1997) 36:1846–1851).

Accordingly, it would be advantageous to provide a mutant form of the modular polyketide synthesis system which cannot employ the natural starter unit. Such systems can be induced to make novel polyketides by supplying, instead, a suitable diketide as an NAC thioester or other suitable thioester. Mutations have been made in the past to eliminate the competition from natural materials (Daum, S. J. et al., *Ann. Rev. Microbiol.* (1979) 33:241–265). Novel avermectin derivatives have been synthesized using a randomly generated mutant strain of the avermectin producing organism (Dutton, C. J. et al., *Tetrahedron Letters* (1994) 35:327–330; Dutton, C. J. et al., *J. Antibiot.* (1991) 44:357–365). This strategy is, however, not generally applicable due to inefficiencies in both mutagenesis and incorporation of the substrates.

Thus, there is a need for a more efficient system to prepare novel polyketides by inhibiting competitive production of the natural product.

DISCLOSURE OF THE INVENTION

The invention is directed to methods to prepare novel polyketides using modified modular polyketide synthase systems wherein directed modification incapacitates the system from using its natural starting material. Novel polyketides can then be synthesized by overriding the starter module and supplying a variety of suitable diketide substrates.

Thus, in one aspect, the invention is directed to a method to prepare a novel polyketide which method comprises providing a thioester diketide substrate to a modular PKS comprising at least two modules under conditions wherein said substrate is converted by said modular PKS to a product polyketide, wherein said PKS has been modified to prevent its utilization of the native starter unit. In other aspects, the invention is directed to the modified modular PKS which is disarmed with respect to utilization of the native starter substrate supplying the initial two carbon unit, and to suitable cells modified to contain this disarmed PKS. The invention is further directed to recombinant materials for production of the modified PKS and to the novel polyketides produced by this system.

MODES OF CARRYING OUT THE INVENTION

Figure 1:
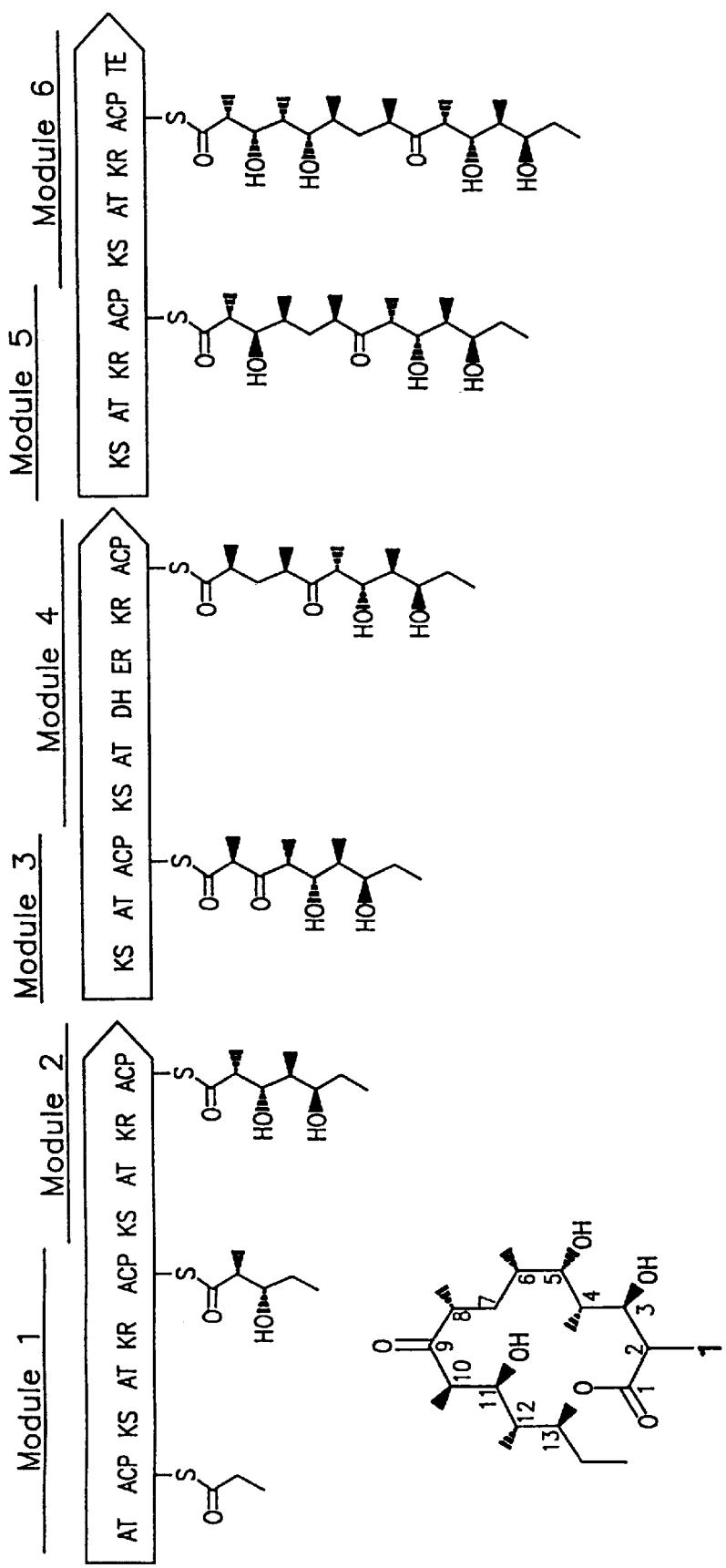
FIG. 1 shows a schematic representation of the DEBS modular PKS.

The invention provides modular PKS systems which are disarmed with respect to loading the native starting material and their corresponding genes. In a particularly preferred embodiment, the ketosynthase (KS) of module 1 is inactivated so as to prevent competition from the native starter unit. Other approaches to similarly disarming the PKS involve inactivating the acyl transferase (AT) or acyl carrier protein (ACP) functions of module 1.

The PKS of the invention must contain at least two modules but may contain additional modules and, indeed, be complete synthase systems. While the DEBS PKS system is used to illustrate the invention, any modular PKS can be used, such as the modular PKS resulting in the production of avermectin, rapamycin and the like. Suitable mutations can be introduced by known site specific mutagenesis techniques.

Other micro-organisms such as yeast and bacteria may also be used. The novel polyketides may be synthesized in a suitable hosts, such as a Streptomyces host, especially a Streptomyces host modified so as to delete its own PKS. The polyketides may also be synthesized using a cell-free system by producing the relevant PKS proteins recombinantly and effecting their secretion or lysing the cells containing them. A typical cell-free system would include the appropriate PKS, NADPH and an appropriate buffer and substrates required for the catalytic synthesis of polyketides. To produce the novel polyketides thioesters of the extender units are employed along with the thioester of a diketide.

The following examples are intended to illustrate but not to limit the invention.

Preparation A

STARTING MATERIALS

*Streptomyces coelicolor* CH999, which has been engineered to remove the native PKS gene cluster is constructed as described in WO 95/08548. pRM5, a shuttle plasmid used for expressing PKS genes in CH999 was also described in that application. Plasmid pCK7 which contains the entire DEBS modular system was described in the foregoing application as well.

EXAMPLE 1

Preparation of DEBS 1+2+TE

A modified DEBS PKS system containing only modules 1 and 2 and thioesterase (TE) activity, designated DEBS 1+2+TE, was subjected to site directed mutagenesis to inactivate module 1 KS by replacing the active site cysteine residue in the signature sequence in which a cysteine residue is followed by three consecutive serine residues followed by a leucine residue by alanine. The resulting expression plasmid, designated pKAO179, encodes a 2-module PKS which is inactive under the standard reaction conditions for synthesis of the native product, i.e., propionyl-CoA, methylmalonyl-CoA, and NADPH. The details of this construction are set forth in Kao, C. M. et al, Biochemistry (1996) 35:112363–12368. When provided with the diketide thioester (2S, 3R)-2-methyl-3,3-hydroxy-pentanoyl-N-acetylcysteamine thioester, and with methylmalonyl-CoA, and NADPH, the triketide product is obtained.

The triketide product is produced under these conditions when the PKS is incubated in a cell-free system or can be duplicated in vivo by providing the appropriate diketide thioester analogs to actively growing cultures of CH999 containing the modified expression plasmid.

A culture of *S. coelicolor* CH999/pKAO179 is established by inoculation of 200 mL of SMM medium (5% PEG-800, 0.06% $MgSO_4$, 0.2% $(NH_4)_2SO_4$, 25 mM TES, pH 7.02, 25 mM $KH_2PO_4$, 1.6% glucose, 0.5% casamino acids, trace elements) with spores. The culture is incubated at 30° C. with shaking at 325 rpm. A solution of (2S, 3R)-2-methyl-3-hydroxypentanoyl N-acetylcysteamine thioester (100 mg) and 4-pentynoic (15 mg) in 1 mL of methylsulfoxide is added to the culture in three parts: after 50 hours (400 µL); after 62 hours (300 µL); and after 86 hours (300 µL). After a total of 144 hours, the culture is centrifuged to remove mycelia. The fermentation broth is saturated with NaCl and extracted with ethyl acetate (5×100 mL). The combined organic extract is dried over $Na_2SO_4$, filtered, and concentrated. Silica gel chromatography yields (2R, 3S, 4S, 5R)-2,4-dimethyl-3, 5-dihydroxy-n-heptanoic acid δ-lactone.

EXAMPLE 2

Preparation of Polyketides from the DEBS Cluster

The active site mutated module 1 KS domain of the eryAI (DEBS 1) gene is provided on a derivative of pCK7 (Kao, C. M., et al., *Science* (1994) 265:409–412), which contains the eryAI, eryAII (DEBS 2), and eryAIII (DEBS 3) genes under control of the actI promoter. Expression from this derivative plasmid named pJRJ2 results in a suitably modified full length PKS system. pJRJ2 was transformed into CH999 and grown on R2YE medium. No detectable 6-dEB-like products were produced.

In more detail, lawns of CH999/pJRJ2 were grown at 30° C. on R2YE agar plates containing 0.3 mg/ml sodium propionate. After three days, each agar plate was overlayed with 1.5 mL of a 20 mM substrate solution in 9:1 water-:DMSO. After an additional 4 days, the agar media (300 mL) were homogenized and extracted three times with ethyl acetate. The solvent was dried over magnesium sulfate and concentrated. Concentrated extracts were purified by silica gel chromatography (gradient of ethyl acetate in hexanes) to afford products.

However, when substrate 2, prepared by the method of Cane et al., *J. Am. Chem. Soc.* (1993) 115:522–526; Cane, D. E. et al., *J. Antibiot.* (1995) 48:647–651, shown in FIG. 2 (the NAC thioester of the native diketide) was added to the system, the normal product, 6 dEB was produced in large quantities. Administration of 100 mg substrate 2 to small scale cultures (300 ml grown on petri plates as described above resulted in production of 30 mg 6 dEB, 18% yield.

EXAMPLE 3

Production of Novel Polyketides

Figure 2:
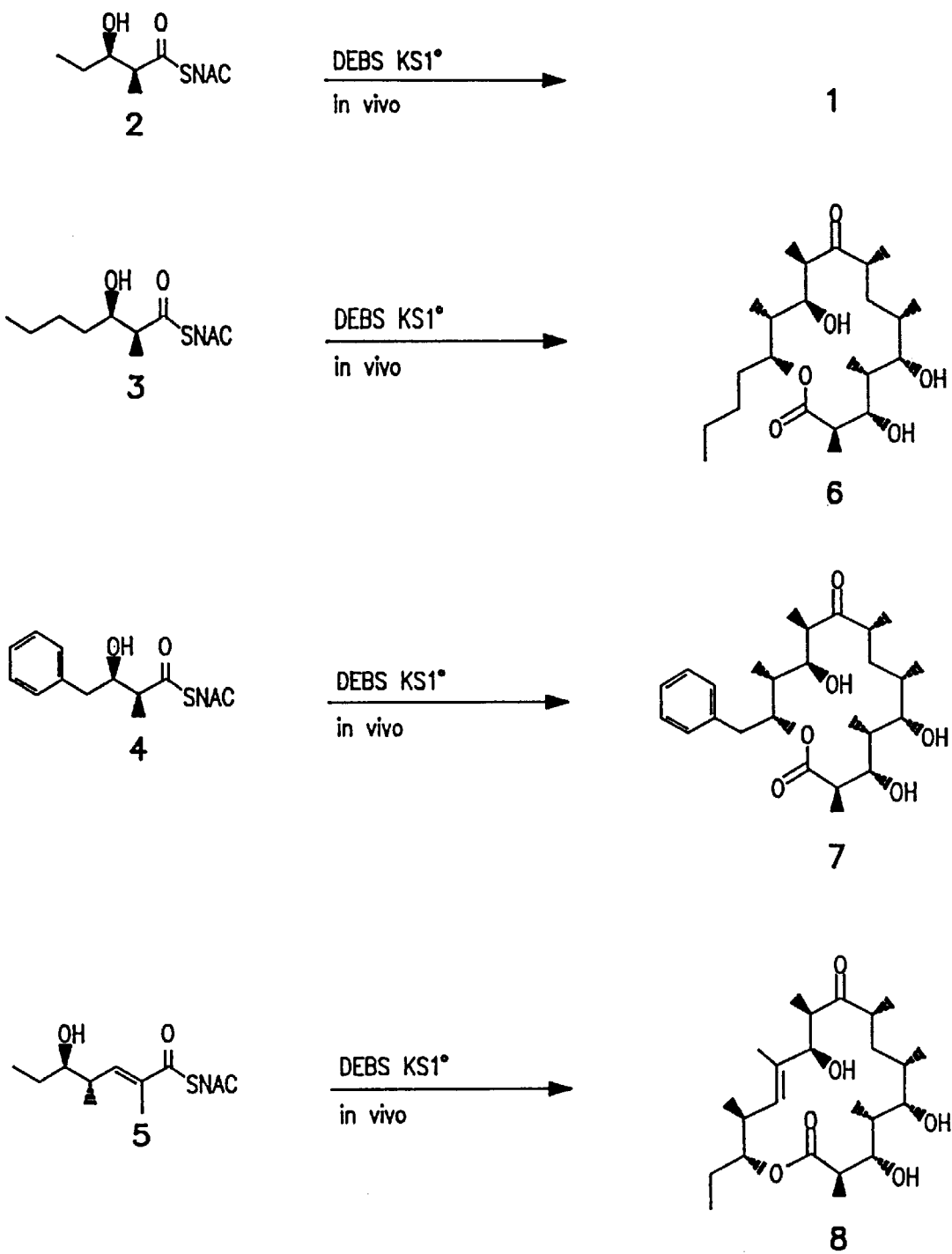
FIG. 2 shows the products of a modified DEBS construct wherein the ketosynthase in module 1 is disarmed.

Diketides with the structures shown in FIG. 2 as formulas 3, 4, and 5 were then administered to growing cultures of CH999/pJRJ2 under the conditions of Example 2. Substrates 3 and 4 were prepared as described for Substrate 2 but substituting valeraldehyde and phenylacetaldehyde, respectively for propionaldehyde in the aldol reactions. The preparation of Substrate 5 was described by Yue, S. et al., *J. Am. Chem. Soc.* (1987) 109:1253–1255. Substrates 3 and 4 provided 55 mg/L of product 6 and 22 mg/L of product 7 respectively. Substrate 5 resulted in the production of 25 mg/L of the 16 member lactone 8, an unexpected product.

EXAMPLE 4

Processing of the Polyketide Products

Figure 3:
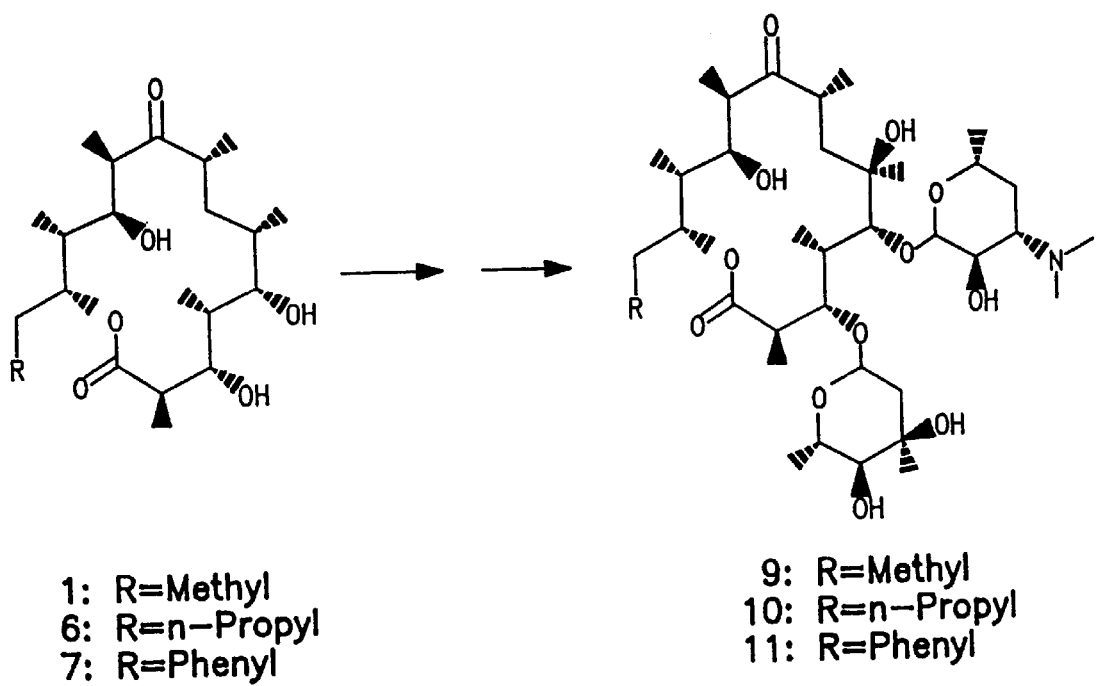
FIG. 3 shows the processing of 6-dEB derivatives to erythromycin-D derivatives.

The successful processing of unnatural intermediates by the "downstream" modules of DEBS prompted an experiment to determine whether the post-PKS enzymes in the erythromycin biosynthetic pathway might also accept unnatural substrates. In the natural producer organism, *Saccharopolyspora erythraea*, 6dEB undergoes several enzyme-catalyzed transformations. Oxidation at C6 and glycosylations at C3 and C5 afford erythromycin D (formula 9 in FIG. 3) and subsequent transformations afford erythromycins A, B, and C. *S. erythraea* mutant (A34) (Weber, J. M. et al., *J. Bacteriol.* (1985) 164:425–433) is unable to synthesize 6dEB. This strain produces no erythromycin when grown on R2YE plates (as judged by the ability of extracts to inhibit growth of the erythromycin-sensitive bacterium *Bacillus cereus*). However, when 6dEB (which has no antibacterial activity) is added to the culture medium, extracts exhibited potent antibacterial activity.

Samples of 6dEB derivatives 6 and 7 were assayed for conversion by this strain. Partially purified extracts demonstrated inhibition of *B. cereus* growth, and mass spectrometry was used to identify the major components of the extracts as formula 10 in FIG. 3 (from 6) and formula 11 (from 7).

In more detail, purified 6 and 7 (5 mg dissolved in 7.5 nm 50% aqueous ethanol) were layered onto R2YE plates (200 mL media/experiment) and allowed to dry. *S. erythraea A34* was then applied so as to give lawns. After 7 days of growth, the media were homogenized and extracted three times with 98.5:1.5 ethyl acetate:triethylamine. Pooled extracts from each experiment were dried over magensium sulfate and concentrated. Extracts were partially purified by silica gel chromatography (gradient of methanol and triethylamine in chloroform). The partially purified extracts were examined by TLC and mass spectrometry. For antibacterial activity analysis, filter discs were soaked in 400 $\mu$M ethanolic solutions of erythromycin D, 10 and 11, as well as a concentrated extract from *S. erythraea A34* which had been grown without addition of any 6-dEB analogs. Disks were dried and laid over freshly-plated lawns of *Bacillus cereus*. After incubation for 12h at 37° C., inhibition of bacterial growth was evident for all compounds but not for the control extract.

What is claimed is:

1. Recombinant host cells which contain a polyketide synthase (PKS), gene cluster which encodes a functional modified modular PKS containing at least a first and second module wherein said gene cluster has been modified so that the PKS encoded is unable to utilize a starter unit used by said modular PKS in unmodified form, but is able to incorporate a diketide into at least a triketide, said gene cluster operably linked to control sequences for expression, wherein at least one of said gene cluster and said control sequences is heterologous to said cells, wherein said modification inactivates the ketosynthase (KS) catalytic domain of the first module, wherein said inactivation is by modification of a single codon of said catalytic domain, wherein said codon, in its unmodified form, encodes cysteine, and wherein said codon in its modified form encodes alanine.

2. The cells of claim 1 wherein said modules are modules of the erythromycin PKS gene cluster, 6-deoxyerythronolide B (6-dEB) synthase.

3. A recombinant plasmid vector which comprises an expression system for production of polyketide synthase (PKS) wherein said expression system comprises a nucleotide sequence encoding a functional modified modular PKS operatively linked to control sequences for expression of said modified PKS containing at least a first and second module, wherein said nucleotide sequence has been modified so that the PKS encoded is unable to utilize a starter unit used by said modular PKS in unmodified form, but is able to incorporate a diketide into at least a triketide, wherein said modification inactivates the ketosynthase (KS) catalytic domain of the first module, wherein said inactivation is by modification of a single codon of said catalytic domain, wherein said codon, in its unmodified form, encodes cysteine, and wherein said codon in its modified form encodes alanine.

4. The vector of claim 3 wherein said modules are modules of the erythromycin PKS gene cluster, 6-deoxyerythronolide B (6-dEB) synthase.

5. The vector of claim 3 wherein said control sequences are heterologous to said encoding nucleotide sequence.

6. The vector of claim 4 which is pJRJ2.

7. Recombinant host cells modified to contain the vector of claim 2.

8. The cells of claim 7 that do not express native PKS activity.

9. The cells of claim 7 that are heterologous to the encoding nucleotide sequences.

10. The cells of claim 9 which are of the genus Streptomyces.

11. The cells of claim 10 which are *S. coelicolor*.

12. The cells of claim 11 which are *S. coelicolor* CH999/pJRJ2.

* * * * *

UNITED STATES PATENT AND TRADEMARK OFFICE
CERTIFICATE OF CORRECTION

PATENT NO. : 6,066,721
DATED : May 23, 2000
INVENTOR(S) : Chaitan Khosla et al.

It is certified that error appears in the above-identified patent and that said Letters Patent is hereby corrected as shown below:

Title page,
Item [56], References Cited, OTHER PUBLICATIONS, please add the following references:

-- Pieper, R., et al., "Remarkably Broad substrate Specificity of a Modular Polyketide Synthase in a Cell-Free System," *J Am Chem Soc* (1995) 117(45):11373-11374.

Pieper, et al., "Cell-free synthesis of polyketides by recombinant erythromycin polyketide synthesis," *Nature* (1995) 378:263-266.

Pieper, et al., "Erythromycin Biosynthesis: Kinetic Studies on a Fully Active Modular Polyketide Synthase Using Natural and Unnatural Substrates," *Biochemistry* (1996) 35:2054-2060.

Pieper, et al., "Purification and Characterization of Bimodular and Trimodular Derivatives of the Erythromycin Polyketide Synthase," *Biochemistry* (1997) 36(7): 1846-1851.

Daum S.J., et al., "Mutational Biosynthesis of New Antibiotics," *Ann Rev Microbiol* (1979) 33:241-265.

Dutton, C.J. et al., Avermectin Biosynthesis. Intact Incorporation of a Diketide Chain-Assembly Intermediate into the Polyketide Macrocycle Ring," *Tetrahedron Letters* (1994) 35(2):327-330.

Dutton, C.J., et al., "Novel Avermectins Produced by Mutational Biosynthesis," *The Journal of Antibiotics* (1991) 44(3):357-365. --

UNITED STATES PATENT AND TRADEMARK OFFICE
CERTIFICATE OF CORRECTION

PATENT NO.   : 6,066,721
DATED        : May 23, 2000
INVENTOR(S)  : Chaitan Khosla et al.

It is certified that error appears in the above-identified patent and that said Letters Patent is hereby corrected as shown below:

Column 5,
Line 41, delete comma between "(PKS)" and "gene".

Column 6,
Line 39, delete "claim 2" and insert -- claim 3 --.
Lines 44-45, delete "Streptomyces" and insert -- *Streptomyces* --.

Signed and Sealed this

Twenty-fourth Day of September, 2002

*Attest:*

JAMES E. ROGAN
*Director of the United States Patent and Trademark Office*

*Attesting Officer*